US010284924B2

United States Patent
Dixit

(10) Patent No.: US 10,284,924 B2
(45) Date of Patent: *May 7, 2019

(54) SYSTEM AND METHOD COMMUNICATING BIOFEEDBACK TO A USER THROUGH A WEARABLE DEVICE

(71) Applicant: Zenso, Inc., San Francisco, CA (US)

(72) Inventor: Rohan Dixit, San Francisco, CA (US)

(73) Assignee: Zenso, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/607,618

(22) Filed: May 29, 2017

(65) Prior Publication Data

US 2017/0258328 A1    Sep. 14, 2017

Related U.S. Application Data

(63) Continuation of application No. 15/017,920, filed on Feb. 8, 2016, now Pat. No. 9,699,528.

(60) Provisional application No. 62/113,491, filed on Feb. 8, 2015.

(51) Int. Cl.
| | | |
|---|---|---|
| *H04Q 9/00* | (2006.01) | |
| *G08B 21/04* | (2006.01) | |
| *A61B 5/00* | (2006.01) | |
| *A61B 5/024* | (2006.01) | |
| *A61B 5/0482* | (2006.01) | |
| *G06F 19/00* | (2018.01) | |
| *G08B 6/00* | (2006.01) | |

(52) U.S. Cl.
CPC ............. *H04Q 9/00* (2013.01); *A61B 5/0004* (2013.01); *A61B 5/0024* (2013.01); *A61B 5/02405* (2013.01); *A61B 5/0482* (2013.01); *A61B 5/486* (2013.01); *A61B 5/7455* (2013.01); *G06F 19/00* (2013.01); *G08B 21/0423* (2013.01); *G08B 6/00* (2013.01); *H04Q 2209/823* (2013.01)

(58) Field of Classification Search
CPC . A61B 5/0004; A61B 5/0024; A61B 5/02405; A61B 5/0482; A61B 5/486; A61B 5/7455; G08B 21/0423
See application file for complete search history.

(56) References Cited

U.S. PATENT DOCUMENTS

| | | | | |
|---|---|---|---|---|
| 2008/0035147 A1* | 2/2008 | Kirby | ................ | A61M 16/0051 128/204.21 |
| 2010/0079264 A1* | 4/2010 | Hoellwarth | ............. | G06F 3/041 340/407.2 |
| 2014/0081666 A1* | 3/2014 | Teller | ..................... | A61B 5/411 705/3 |
| 2015/0199010 A1* | 7/2015 | Coleman | .............. | A61B 5/0006 345/156 |

FOREIGN PATENT DOCUMENTS

WO    WO 2014040175 A1 *    3/2014    ........... A61B 5/0006

* cited by examiner

*Primary Examiner* — Nader Borlourchi
(74) *Attorney, Agent, or Firm* — Brian Van Osdol; Alpine Patents LLC

(57) ABSTRACT

A system and method for communicating biofeedback to a user through a wearable device that includes collecting physiological data of at least one physiological property of a user; processing the physiological data into at least one biosignal; monitoring the at least one biosignal for a feedback activation condition; and upon satisfying a feedback activation condition, delivering haptic feedback.

14 Claims, 21 Drawing Sheets

Heart Rate Down

HRV

Heart Rate Down + HRV

US 10,284,924 B2

SYSTEM AND METHOD COMMUNICATING BIOFEEDBACK TO A USER THROUGH A WEARABLE DEVICE

CROSS-REFERENCE TO RELATED APPLICATIONS

This application is a continuation application of U.S. patent application Ser. No. 15/017,920, filed on 8 Feb. 2016, which claims the benefit of U.S. Provisional Application No. 62/113,491, filed on 8 Feb. 2015, both of which are incorporated in their entireties by this reference.

TECHNICAL FIELD

This invention relates generally to the field of biofeedback devices, and more specifically to a new and useful system and method for communicating biofeedback to a user through a wearable device.

BACKGROUND

Higher levels of heart rate variability have been shown to have a relationship to lower stress levels. Traditional approaches in biofeedback have used obtrusive techniques to train higher amounts of heart rate variability. In some cases, these techniques are limited to laboratory or controlled environments as a result of how feedback was delivered. Such problems exist in other fields of biofeedback as well. Thus, there is a need in the biofeedback field to create a new and useful system and method for communicating biofeedback to a user through a wearable device. This invention provides such a new and useful system and method.

DESCRIPTION OF THE EMBODIMENTS

The following description of the embodiments of the invention is not intended to limit the invention to these embodiments but rather to enable a person skilled in the art to make and use this invention.

1. System for Communicating Biofeedback to a User

Figure 1:
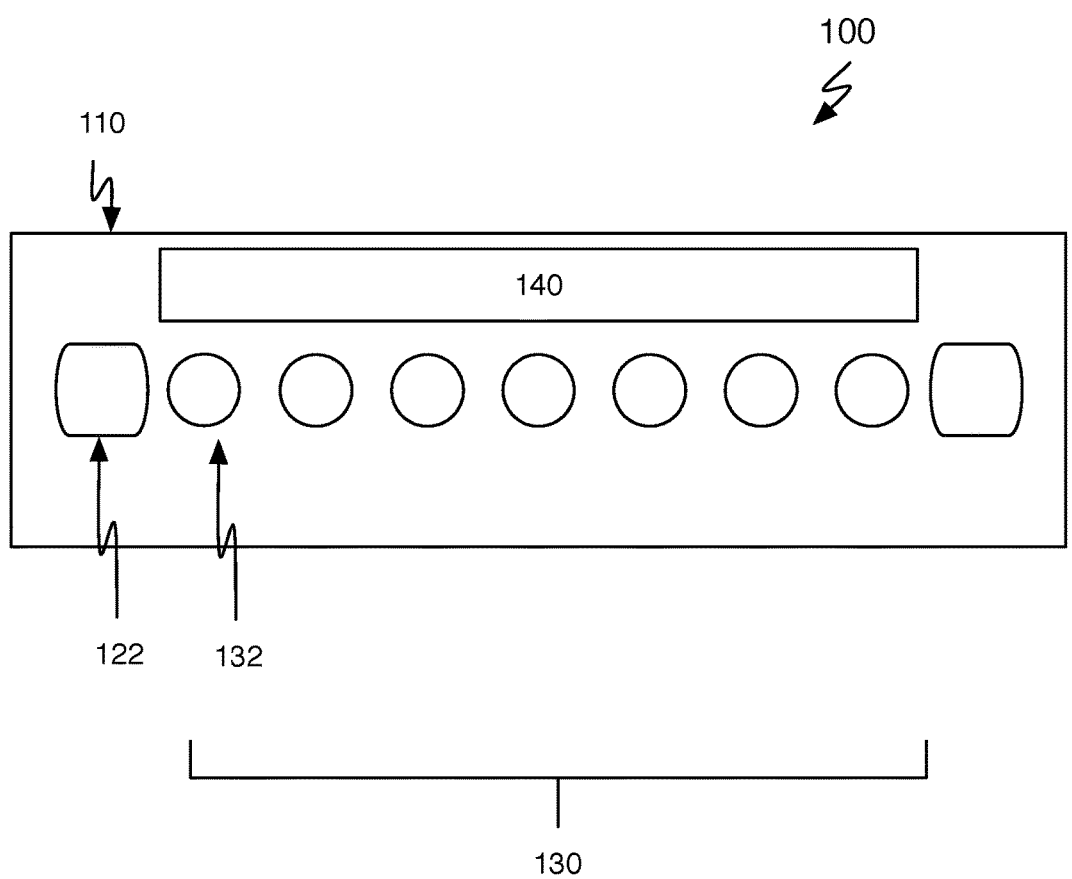
FIGS. 1 and 2 are a schematic representations of a system of a preferred embodiment.
Figure 2:
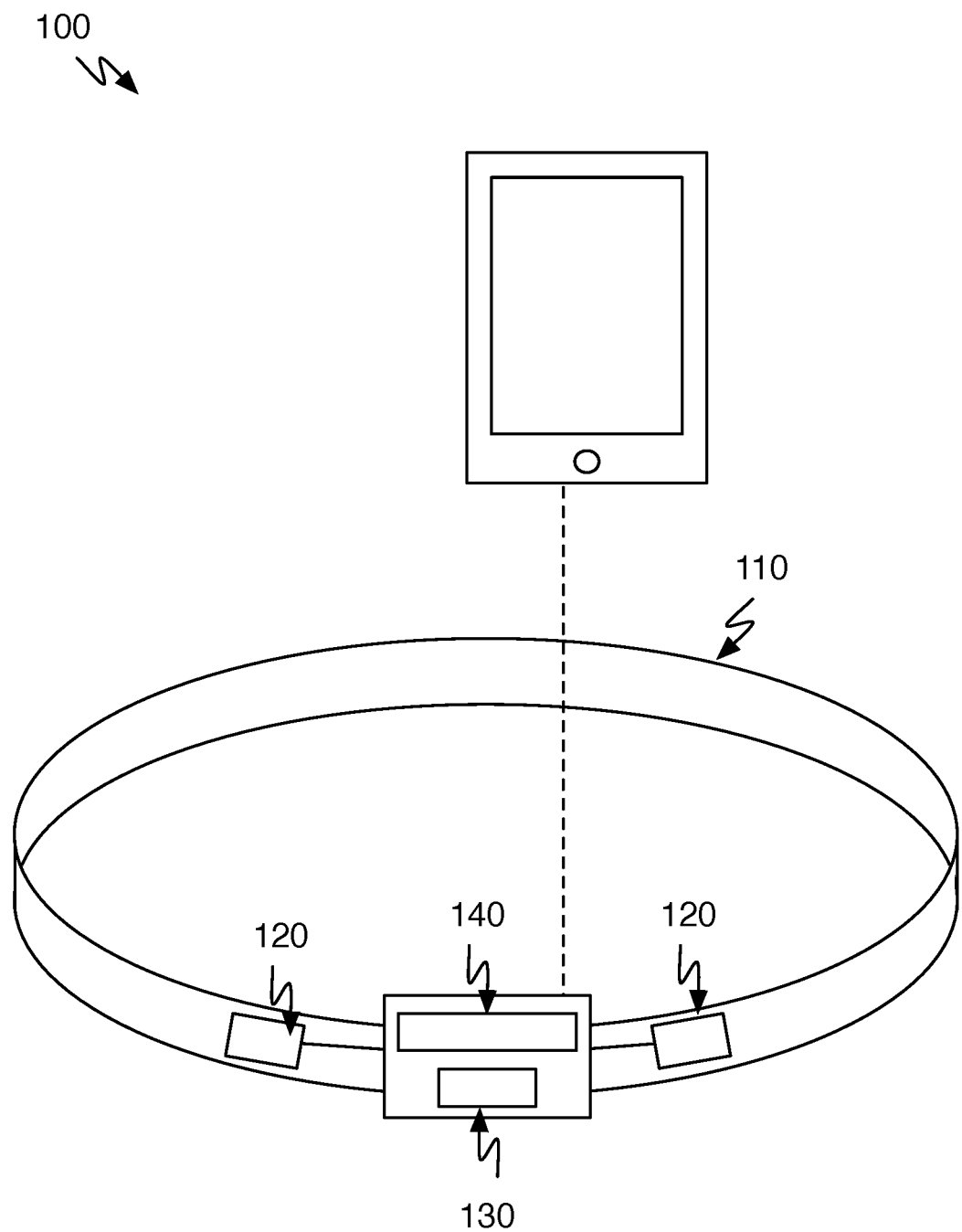

As shown in FIGS. 1 and 2, a system 100 for communicating biofeedback to a user through a wearable device of a preferred embodiment can include an attachment structure 110, at least one biosensor 120, a haptic feedback system 130, and a computing system 140. The system 100 functions to monitor real-time biosensor data and synthesize the biosensor data into active feedback. The biosensor 120 collects physiological data on at least one biosignal, the computing system 140 detects changes in a biosignals that match a pattern or satisfy one of a set of conditions, and the haptic feedback system 130 provides patterns of stimulation to the user. The patterns of stimulation are correlated with the biosignal. The haptic feedback is preferably unobtrusive so as to not interfere with routine activities. As one potential benefit, the user can build an awareness and in some cases control over current internal states using the system 100.

The patterns of biofeedback can be mapped to a variety of different properties or characteristics of one or more biosignals. In one variation, the haptic feedback system 130 is an array of haptic feedback nodes 132, which can enable complex patterns of biofeedback to be delivered. While, the biosignals are typically beneath the awareness of a user, the haptic stimulation is active and detectable. Over time, a user may learn to manipulate these vibrational patterns and in some cases gain a degree of conscious control over physiological properties. The haptic feedback can also be used to alert users to a significant change in their body, communicate internal state to other users, build awareness of emotions, or used for any suitable applications.

In a preferred implementation, the system 100 is used to deliver haptic feedback according to the heart rate variability (HRV) of a user. HRV refers to the variability in heart rate over a given time period. Heart rate varies from beat to beat and high HRV is a general indicator of heart health. HRV is an integral part of an individual's response to variations in physiological and psychological demands and inputs from both internal and external sources. It represents a person's ability to adapt to shifting internal and external states. HRV is influenced by sympathetic and parasympathetic activity within an individual's body. Thus, HRV additionally represents a person's current state of stress or relaxation, with low HRV being related to higher stress states and high HRV being related to lower stress states. In one implementation, the biosensor 120 collects heart beat activity data, which can be used to generate a heart rate signal. The heart rate signal is a time-ordered sequence of data points on real-time calculations of heart rate—the heart rate signal shows the variation of heart rate as a function of time. Haptic feedback is delivered when heart rate variability goes below a particular threshold, which can be an indicator of being stressed, anxious, or nervous. The haptic feedback can be a physical reminder of their internal state, which can lead to mindfulness and as mentioned above changes in physiological state.

Figure 3:
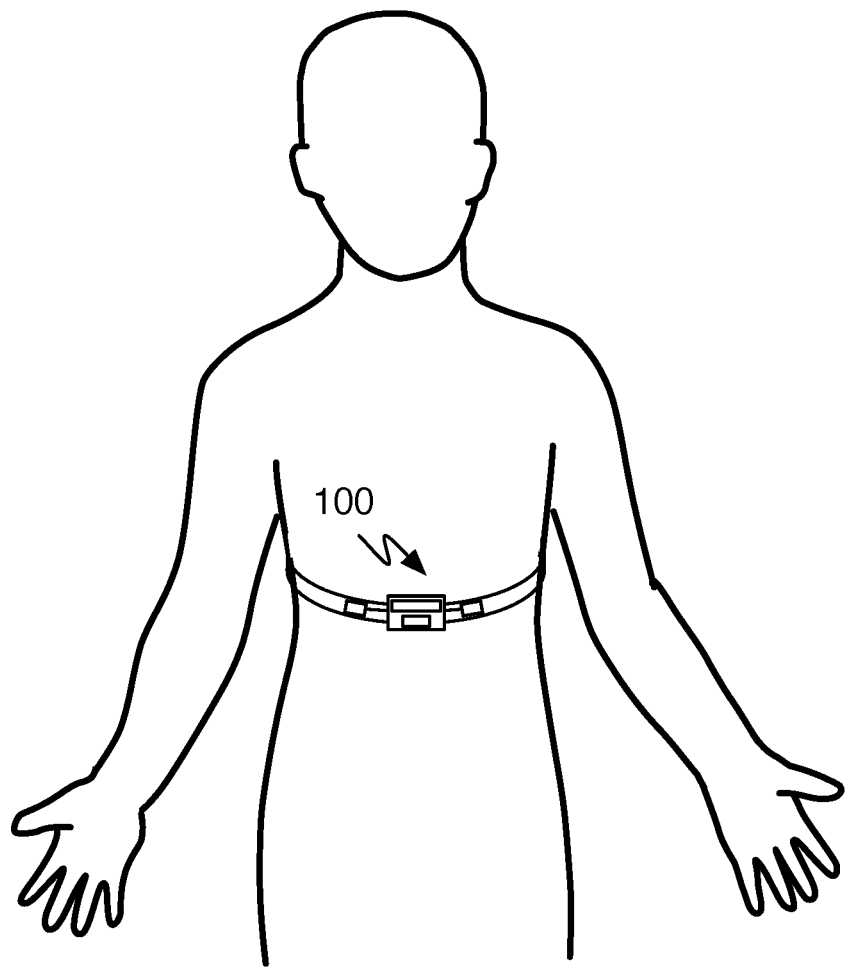
FIG. 3 is a schematic representation of a system worn around the torso.
Figure 4:
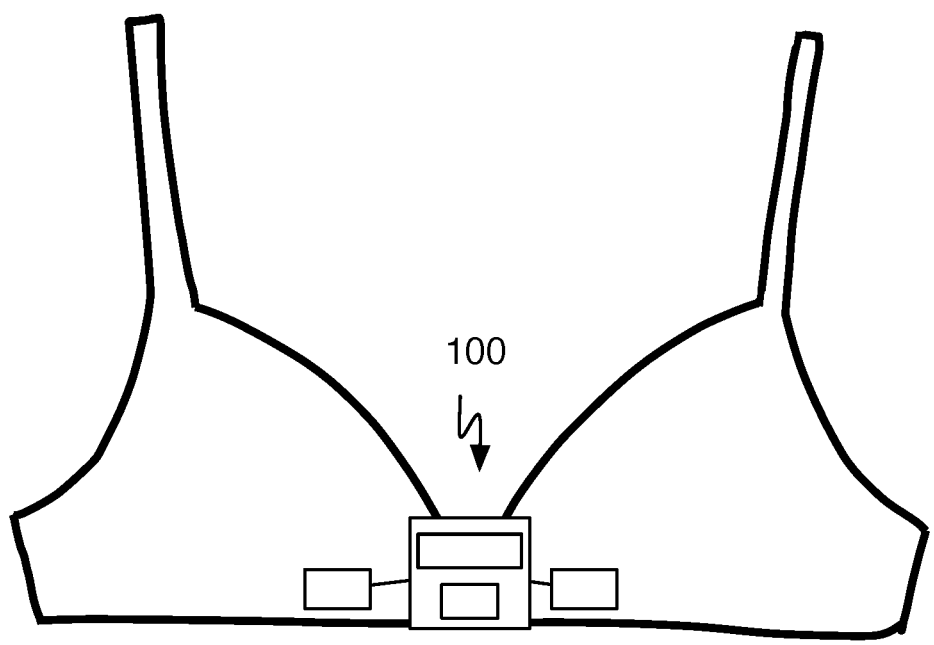
FIG. 4 is a schematic representation of a system integrated into an undergarment.
Figure 5:
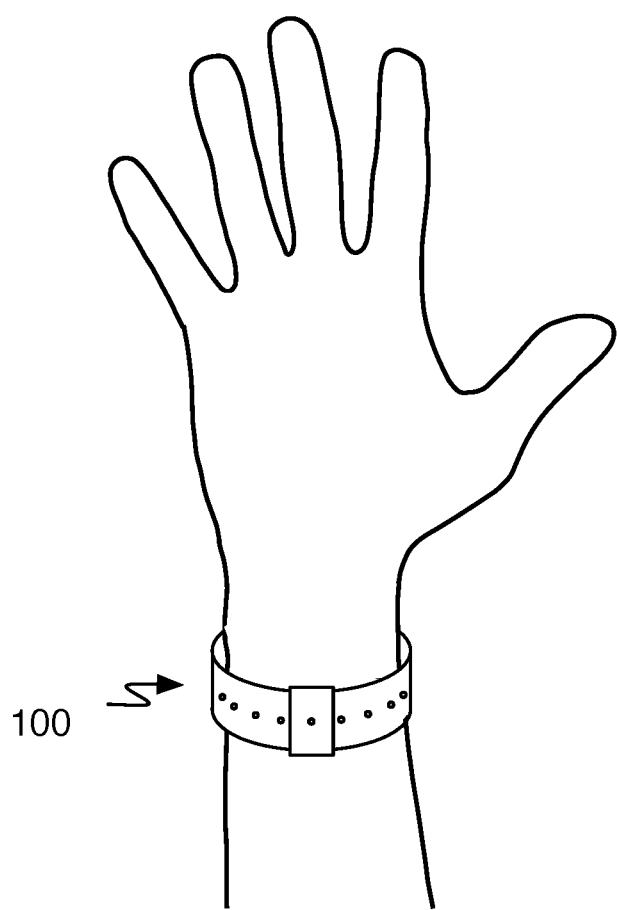
FIG. 5 is a schematic representation of a system worn around the wrist.

As shown in FIG. 3, one exemplary implementation of the system 100 can be a band worn around the torso of the user. The system 100 can also be integrated into a bra as shown in FIG. 4, shirt, or any suitable piece of apparel. In other variations, the system 100 could be a device to be worn on the wrist as shown in FIG. 5, arm, ankle, ear, around the neck, around or on top of the head, or at an suitable location on the body.

Figure 6:
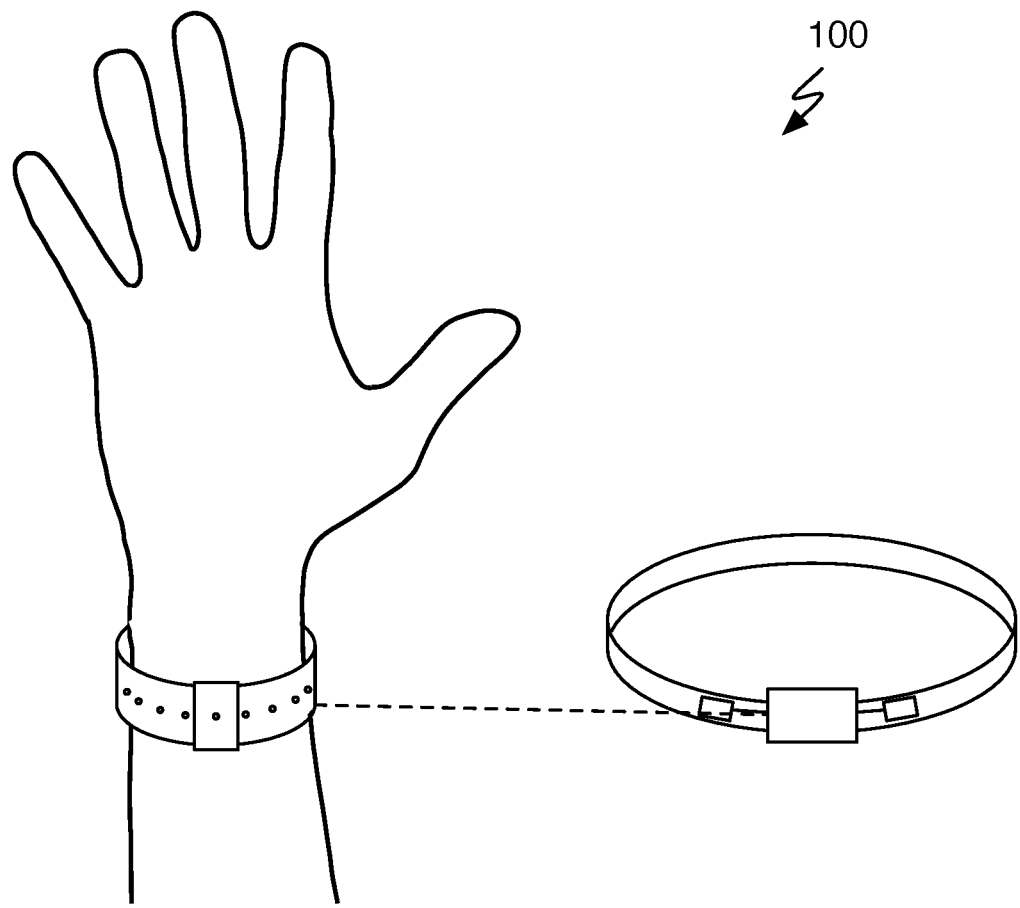
FIG. 6 is a schematic representation of a system with a multiple wearable devices used in combination.

As shown in FIG. 6, another implementation can enable a multi-device approach. Sensing could be performed at one or more sites on the body through at least one device and haptic feedback can be performed at one or more sites by at least a second device. For example, the band may be used for measuring heart activity and a wristband may be used in delivering haptic feedback.

Additionally, the biosensor 120 and/or the haptic feedback system 130 could be an accessory component of a computing device such as a smart watch, smart glasses, or any suitable computing element. Application logic can control such device accessory components in facilitating implementation of the system 100.

The attachment structure no of a preferred embodiment functions to house a set of system components and to physically couple a device to a user when worn. The attachment structure houses at least a subset of components of the system 100. As mentioned above, the system 100 may include multiple devices in which case, the system 100 may include multiple attachment structures no to house their respective components. The attachment structure no can be made of any suitable material and may include a variety of structural geometries. The attachment structure no is preferably a wearable or attachable element that may be configured for coupling to the body at the torso/chest, the wrist, the arm, the neck, the ear, the head, or at any suitable location. The attachment structure can be one of a chest band, a wristband, undergarment (e.g., a bra), head mounted device, ring, necklace, or any suitable wearable item. The attachment structure no can include an adhesive attachment mechanism to stick to a user's body (e.g., an adhesive patch). The attachment structure 110 may alternatively include a clasp so as to be attached or released from the body. For example, a strap may include a variable length clasp so that it can be placed around a user's torso or removed. The attachment structure no may alternatively or additionally include an attachment mechanism such as a clip, button, hoop and loop fastener, magnet, or any suitable attachment mechanism. The attachment mechanism can function to enable the device to be attached to another element such as a third party band or to an undergarment. The attachment structure 110 can use any suitable approach to make a wearable device.

As described above the system 100 may include multiple devices. In a multiple device variation, each device can include attachment structure 110. Herein, a single device variation is described that houses the biosensor 120 and the haptic feedback system 130, but any suitable number of devices with any suitable configuration of biosensors and haptic feedback elements may be used. In one variation, the worn device may attach to another smart garment or object through a connector interface in which case the attachment structure 110 may simply be a cartridge housing the components and interfacing with the other item.

When worn, the attachment structure preferably physically couples the biosensor 120 and the haptic feedback system 130 to a portion of a user's body. The physical coupling may be promoted in regions of the biosensor 120 and the haptic feedback system 130—physical contact with the body may be preferred for operation of some variations of the biosensor 120 (e.g., an ECG sensor) and/or the haptic feedback system 130 (e.g., a vibrational feedback system). Alternatively, the attachment structure no can promote close proximity to a user if direct contact is not needed such as an image-based biosensor 120 or a thermal-based haptic feedback system 130.

The attachment structure no preferably houses a set of device components. In one variation, the attachment structure no includes a cartridge or a body structure that functions as the housing. The attachment structure no can include a housing for the biosensor 120, the haptic feedback system 130, a computing system 140 with any necessary processing, communication, storage, power or other computing components. In one implementation, the attachment structure 110 of one device can include a dry skin electrode system with at least two electrodes 122 to establish contact with a user's skin. The haptic feedback system 130 can be included within a central region of the attachment structure as shown in FIG. 2. The haptic feedback system 130 may alternatively include a set of haptic feedback nodes 132. The haptic feedback nodes 132 can be distributed in a variety of configurations relative to the attachment structure 110. In a variation where the attachment structure 110 is a torso band, the haptic feedback nodes 132 can be positioned along the length of the attachment structure 110 as shown in FIG. 6.

In one implementation, the attachment structure comprises an elastic band that fastens at a cartridge structure. The cartridge structure houses the biosensor 120, the haptic feedback system 130, and the computing system 140. In one variation, the attachment structure includes two conductive snaps that include a mechanical coupling mechanism to connect the elastic band and the cartridge structure. The conductive snaps are additionally conductively coupled to the biosensor.

Figure 8:
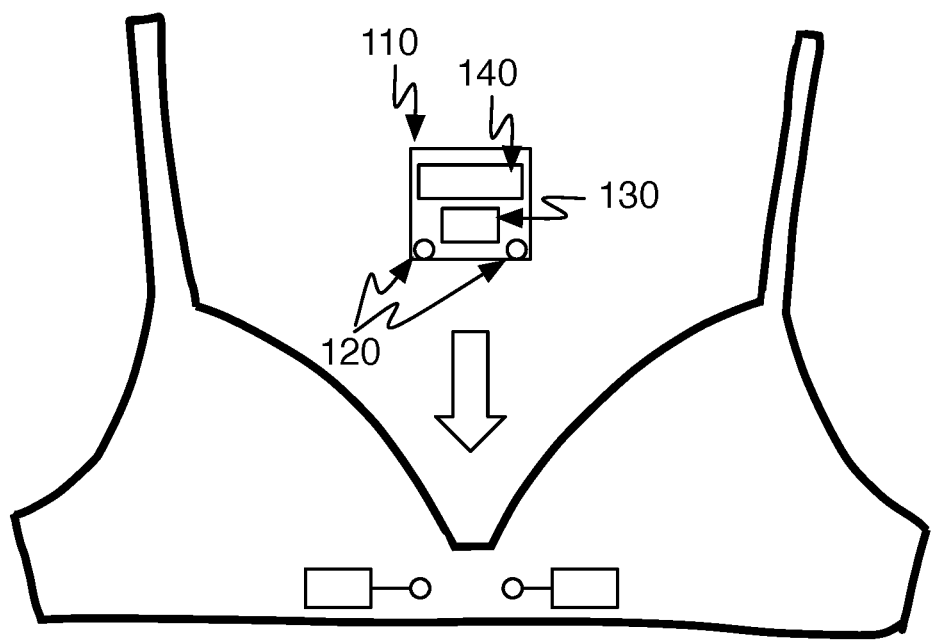
FIG. 8 is a schematic representation of a system with a removable main housing body.

In one implementation, the attachment structure is part of a bra such as a sports bra. Conductive fabric or other suitable garment based electrical components may be used in integrating the biosensors and/or haptic feedback system 130 into the bra. In one variation, the haptic feedback nodes 132 can be distributed along the bottom seam of the bra, and a main housing body can be removably coupled at the front center area of the bra. In another variation, two passive conductive heart rate sensing pads can be integrated into the bra and a main housing body can be removably coupled at the front center area of the bra as as shown in FIG. 8. A conductive connection is established to the integrated sensing pads of the bra.

In yet another implementation, the system 100 may include at least a second attachment structure, which can function to enable the biosensor 120 and the feedback system 130 (or portions of either) to be in distinct locations of the body. A first attachment structure can be worn at a distinct location on the body from the second attachment structure. The heart rate activity sensor can be integrated with one attachment structure and the haptic feedback system 130 can be integrated to the other one. Each of the two devices includes portions of the computing system 140 to facilitate their respective roles. The two devices preferably communicate wirelessly, but a wired connection may additionally be used.

The biosensor 120 of a preferred embodiment functions to sense at least one physiological property of a user. The biosensor 120 can preferably sense the heart activity of a user. The biosensor 120 can be an electrocardiogram (ECG) sensor, an electroencephalogram (EEG) sensor, an electromyography (EMG) sensor, a galvanic skin response (GSR) sensor, a photoplethysmography (PPG) sensor, an infrared spectroscopy (NIRS) sensor, a photoplethysmography (PPG) sensor, and/or a breath sensor. As discussed above, one implementation uses a dry skin electrode system with at least two electrodes that can detect heart activity when in contact with the body 122. The sensed heart activity is preferably used to generate a heart rate signal, which can be used in monitoring heart rate variability (HRV). The heart rate signal can additionally be correlated to breathing rate, but the breathing rate may alternatively be measured or deduced through other biosensing approaches. In one variation, the biosensor 120 is can be an ECG sensor. The magnitude of the Rspike can be correlated to the breathing rate of a user. The Rspike preferably is greater when during an exhaling breath compared to an inhaling breath in part because the sensor positioned on the chest may be physically closer to the heart. Breath may alternatively be sensed directly using a breath sensor which may include an optical system, motion sensor (e.g., an inertial measuring unit IMU) or any suitable type of breath sensor. The biosensor 120 is preferably positioned within the attachment structure 110 to promote a preferred alignment and orientation on the body.

The system 100 can include one or more biosensors 120. The set of biosensors can be of one or multiple types of biosensors 120. The system 100 may additionally be adapted to work in combination with inter-body biosensors, biosensors of another person, or an external sensor such as an imaging system and/or any suitable biosignal or physiological data source. In one variation, a non-biological signal may be used in addition to or in place of a biosignal. An input signal can be user-generated, an environmental signal of interest, or any suitable input signal that is not measured from the input biosensors.

In one variation, the system 100 can additionally include an inertial measurement unit (IMU), which may include one or more accelerometers, gyroscopes, magnetometers, and/or other inertial sensing components. The IMU may be used to acquire activity information for a user. The activity information may be used in directing the operating mode of the system 100. For example, the IMU may be used to detect when the user is participating in strenuous activity, in which case increased heart rate can be attributed to physical activity and not a change in the mental state of the user.

The haptic feedback system 130 of a preferred embodiment functions to provide detectable and unobtrusive feedback to the user. The haptic feedback system 130 is preferably activated by the computing system 140 based on at least the one biosignal. The haptic feedback system 130 is preferably a primary feedback mechanism, but visual, auditory, and/or other tactile feedback systems may be used.

The haptic feedback system 130 is preferably a tactile feedback system that delivers contact stimulation to at least one point on the body. The tactile feedback elements can apply their stimulation through movement of the attachment structure 110 or other elements. The tactile feedback elements may alternatively apply stimulation directly to the body surface of the user. Direct tactile contact can use less energy and be less obtrusive than applying tactile feedback through motion of the attachment structure 110. The haptic feedback system 130 can include actuators such as vibrational elements, protruding elements, tapping elements, and/or any suitable type of tactile feedback element. The haptic feedback system 130 can additionally or alternatively include haptic feedback elements such as a heating element.

In one implementation, the haptic feedback system 130 includes a single haptic feedback element. For example the haptic feedback system 130 can include one vibrational motor. The haptic feedback system 130 more preferably includes a set of haptic feedback elements (i.e., haptic feedback nodes). Herein, vibrational nodes are described as a preferred implementation, but any suitable alternative or additional feedback element may be used.

Figure 7:
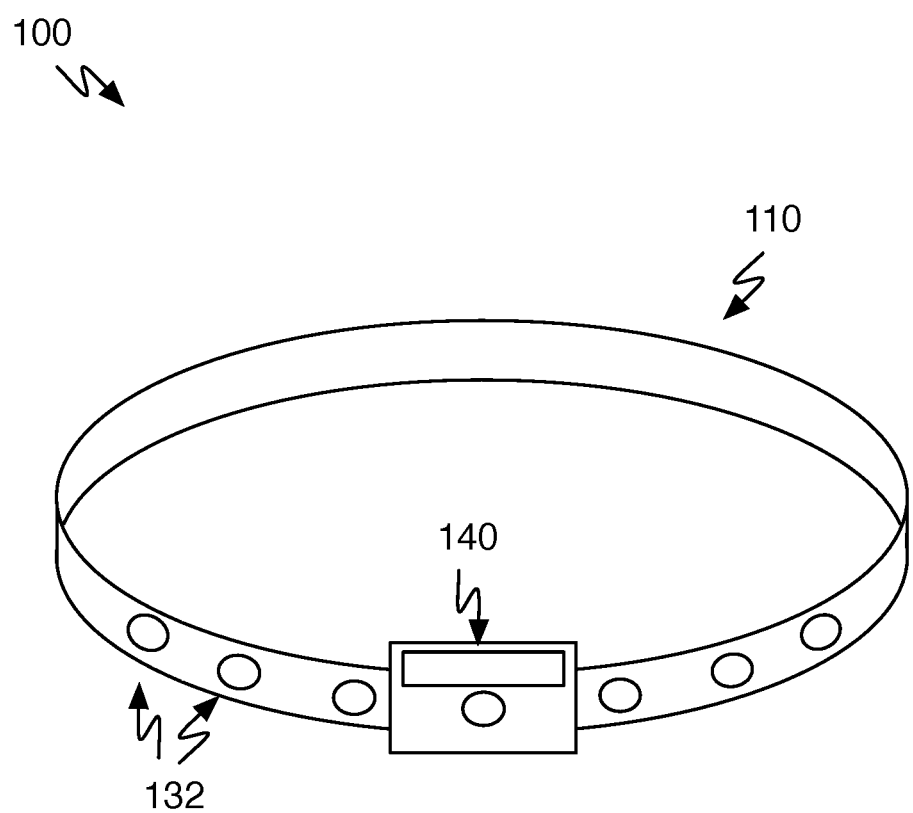
FIG. 7 is a schematic representation of a system with an one dimensional array of haptic feedback nodes.
Figure 9:
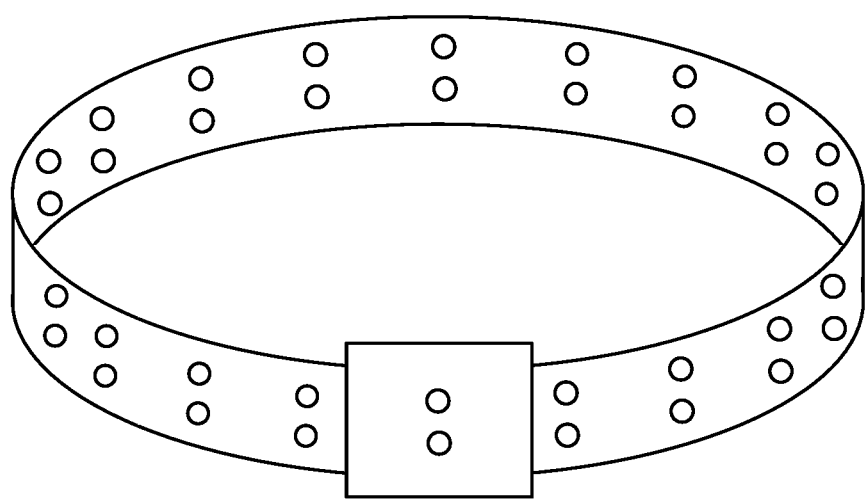
FIG. 9 is a schematic representation of one variation of a 2D array of haptic feedback nodes.
Figure 10:
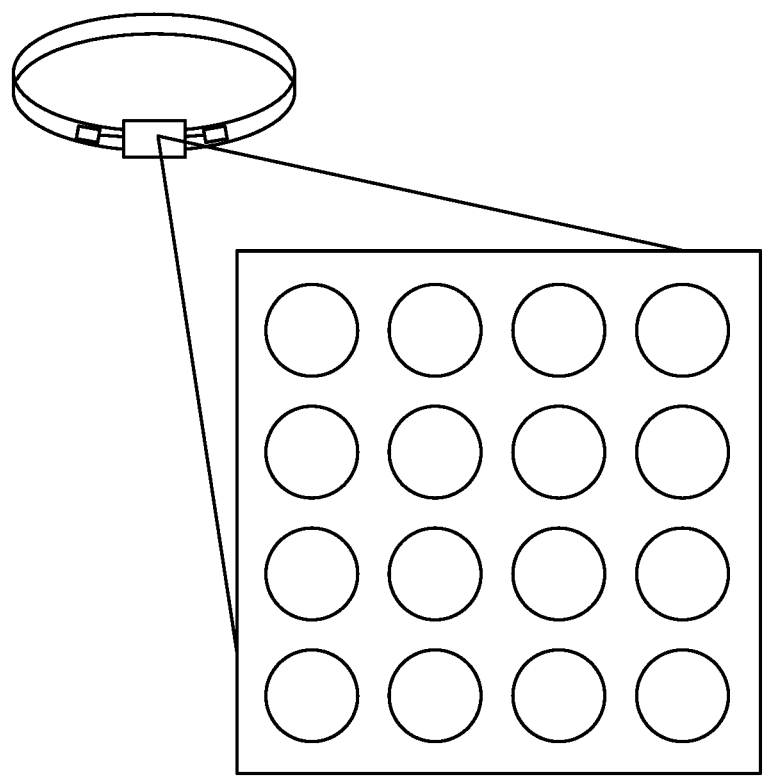
FIG. 10 is a detailed schematic of haptic feedback nodes centralized in a rectangular grid.
Figure 11:
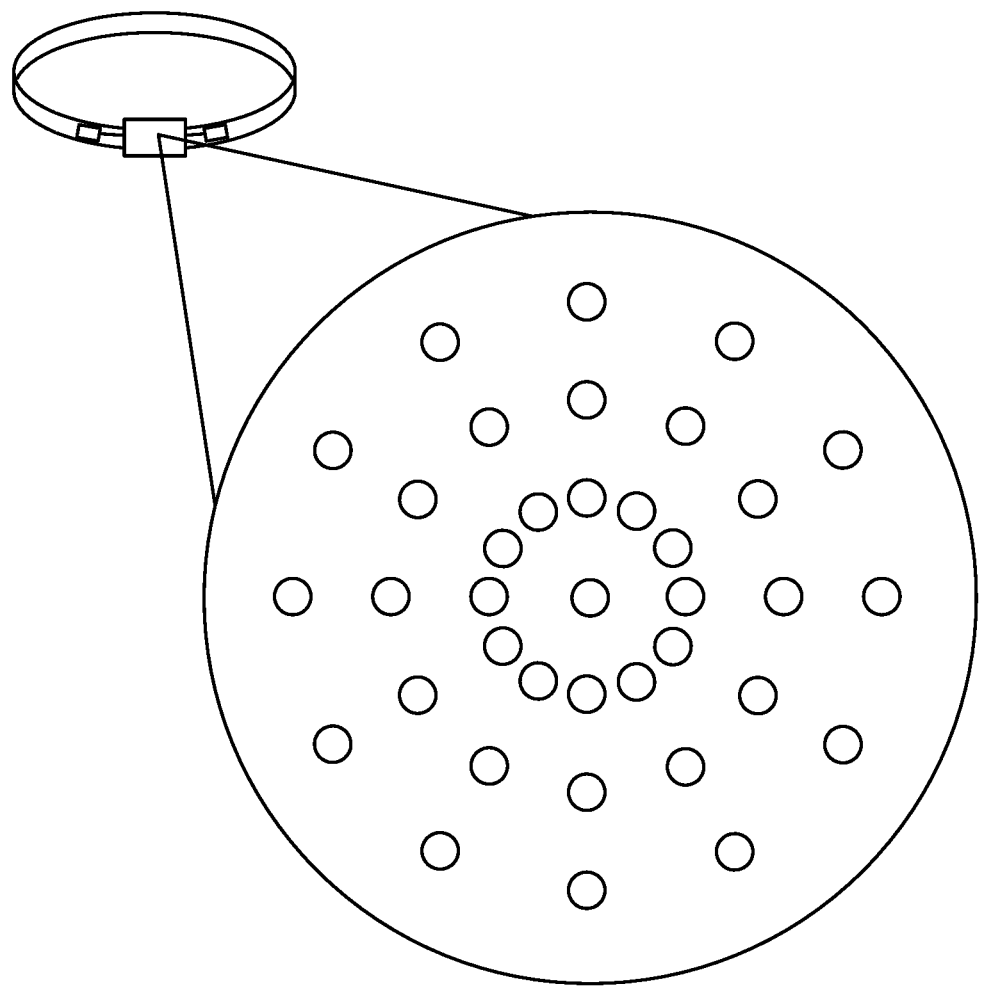
FIG. 11 is a detailed schematic of haptic feedback nodes centralized in a radial grid.

The haptic feedback system 130 preferably includes a set of haptic feedback nodes 132, more specifically a set of vibrational nodes. The set of vibrational nodes can be an array of vibrational elements. The array of vibrational nodes preferably has a particular arrangement and organization. The array of vibrational nodes can be a one-dimensional array. The one-dimensional array of vibrational nodes is substantially arranged in a linear or sequential arrangement as shown in FIG. 7. Activation of the vibrational row nodes may result in a user experiencing directional movement back and forth across the row of vibrational nodes. The array of vibrational nodes can be arranged in a two-dimensional (2D) array. The 2D array may be distributed over a prolonged length of the attachment structure 110 as shown in FIG. 9. The 2D array may alternatively be centralized within a particular region as shown in FIGS. 10 and 11. For example, a circular array of vibrational nodes can enable radial patterns, movement patterns along different axis, and other suitable patterns. There may additionally be multiple discrete 2D arrays of vibrational nodes.

The array of vibrational nodes can be uniformly spaced (i.e., substantially equal spacing between nodes), non-uniformly spaced (i.e., varying spacing between the nodes), continuously spaced (i.e., lacking a distinct break or gap in the array of nodes), discontinuous (e.g., one sub-array of vibrational nodes worn on the wrists and a second sub-array of vibrational nodes worn on a second wrist).

Feedback is delivered by activation and deactivation of these nodes independently or in combination or succession. The computing system 140 can set the haptic feedback system 130 into an activation mode that sequentially activates a subset of haptic feedback nodes 132 in the array of haptic feedback nodes 132. Users may experience successive transitions between vibrational nodes in the array as directional movement along their skin. In a particular implementation, the haptic feedback system 130 may leverage the cutaneous rabbit illusion approach, which creates the perception of seamless motion across the skin between discrete vibratory nodes. The array of vibrational nodes are preferably stimulated according to the at least one biosignal. The timing, intensity, location, and other properties of stimulation patterns can be used in generating distinct feedback. For example, the temporal component of the pattern, which may impact the sensation of how the perceivable vibration moves along the device, can be proportional to the magnitude of a biosignal.

In one variation the array of nodes can include feedback of at least two types. For example, two types of vibrational nodes may be used in the array of vibrational nodes. In another example, a tactile feedback node can be used in addition to a heat-based feedback node.

The computing system 140 of a preferred embodiment functions to manage operation of the system 100. The computing system 140 is preferably housed within the attachment structure no. The computing system 140 can include a processor (e.g., a microprocessor), storage, communication module(s) (e.g., Bluetooth, Wi-Fi, cellular data module, etc.), component drivers (e.g., biosensor driver circuitry and haptic feedback driver circuitry), power system, and/or any suitable components to facilitate operation. The power system could be any suitable type of battery or source of power such as a rechargeable and/or removable battery. The power source element could additionally include a recharging element for recharging the power source. The communication module can be a wireless transmitter that may send and/or receive data with a plurality of external devices, i.e. smartphones, computers, or other devices. In one variation auditory, visual or tactile feedback for the user is displayed by an external device, like a mobile phone, tablet or desktop computer. The feedback can be communicated with the wireless transmitter The computing system 140 is used to receive, store, and analyze physiological data to generate at least one biosignal. The at least one biosignal preferably includes a heart rate signal. The computing system 140 additionally manages the activation of the haptic feedback system 130. In one variation, activation of the haptic feedback system 130 is based in part on the heart rate variability in the heart rate signal. The computing system 140 can analyze vital sign data from the biosensor 140 and determines appropriate haptic feedback to provide to users. The computing system 140 also determines appropriate feedback to provide to users based on comparing stored vital sign parameters with a users current vital sign parameters. The computing system 140 can additionally set the operational mode and drive the haptic feedback system 130 according to the appropriate feedback. The computing system 140 is configured to transmit both activating and deactivating signals to the haptic feedback nodes 132 based on previously determined feedback criteria. The computing system 140 can additionally manage power, communication, and other suitable computing operations on the device.

The system 100 preferably includes a variety of operational modes. The operational modes can be set or partially determined through user input, environmental conditions, and/or other properties. In one implementation, the system 100 includes a user control system on the device through which the user can specify different operating modes. In another implementation, the selectable modes. The user control system can be physical user input elements on the device, but may alternatively be directives communicating from a secondary computing device such as a smart phone, tablet, or computer. In another implementation, the activity of the user detected by an IMU can be used to activate and suspend biofeedback depending on detected activity of the user. In another implementation, the selectable modes are controlled at least in part by electromyographic (EMG) muscle input sensor/s embedded in the strap.

Figure 12A:
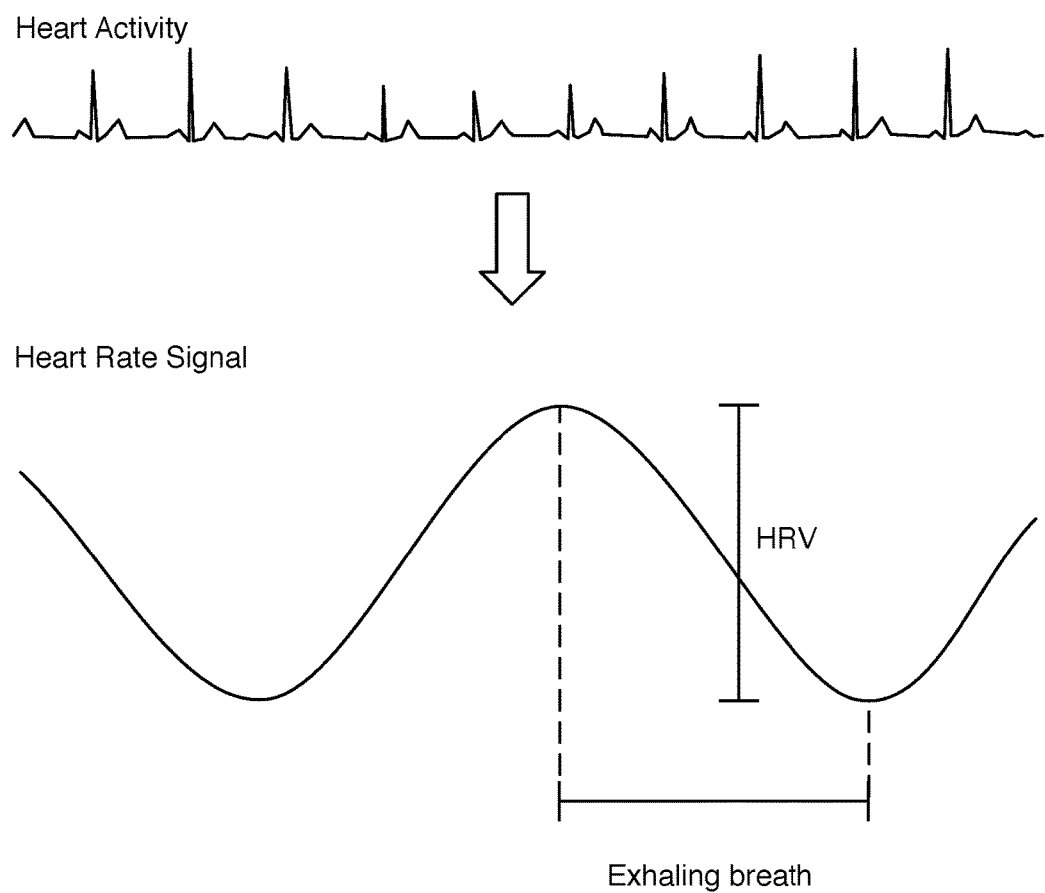
FIGS. 12A and 12B are schematic representations of converting monitored physiological data into a biosignal used for delivering feedback.

The system 100 preferably includes a monitoring mode, wherein the biosignals are monitored. The biosensor 120 collects physiological data and the computing system 140 processes the data. Preferably, the physiological data is heart rate data. A heart signal is preferably a real-time analysis of heart rate as a function of time. The heart rate signal will generally have an oscillating property. The variance of the heart rate signal within a localized sample is the heart rate variance as shown in FIG. 12A. HRV can be correlated to the mental state of the user including anxiety and stress levels. The cyclical heart rate variability additionally maps to the breathing patterns of a user as additionally shown in FIG. 12A. Active feedback can be delivered in synchronization with the heart signal to guide the breathing of the user. In one variation, the system 100 can activate a feedback mode when the HRV is below a particular threshold. In another variation, machine learning can be applied to classifying and detecting various patterns in the heart rate signal and/or other biosignals that correlate with particular mental states.

Figure 12B:
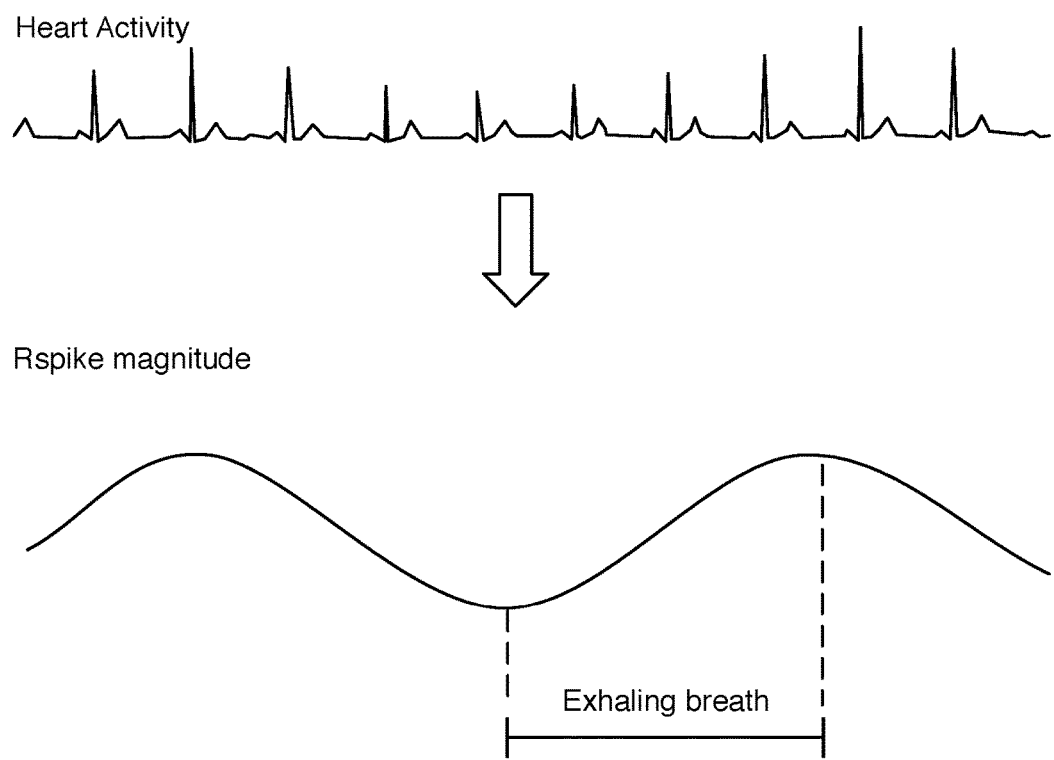

In another variation, the monitoring mode can monitor the magnitude of the Rspike portion of an ECG signal. As discussed above, the Rspike may have greater magnitude during an exhaling breath with the greatest Rspike magnitude at the end of an exhale (i.e., when the ECG sensor is closest to the heart). As shown in FIG. 12B, a breathing rate signal can be generated from the ECG signal.

In a feedback mode, the haptic feedback system 130 is activated. The haptic feedback system 130 can be driven in a variety of patterns. The magnitude, the duration, the sequence or pattern, transition between different feedback nodes, combination of types of haptic feedback, and other properties of the haptic feedback system 130 can be used to signal different attributes to the user.

In one variation, the vibratory output of a haptic feedback system 130 can be set stronger or weaker depending on the physiological signal being measured. For example, the magnitude of vibration can be proportional to the magnitude of the HRV signal. Similarly a feedback pattern can be used to convey some information.

In a variation with an array of haptic feedback nodes 132, the activated feedback nodes can provide alternative ways of communicating information. For example, in a 1D array of vibratory nodes positioned around a band, the activated feedback node can provide information to the user. For example, different information may be conveyed to a user depending on if the active feedback node is located in the front, right, left, back, or any suitable location.

Figure 13:
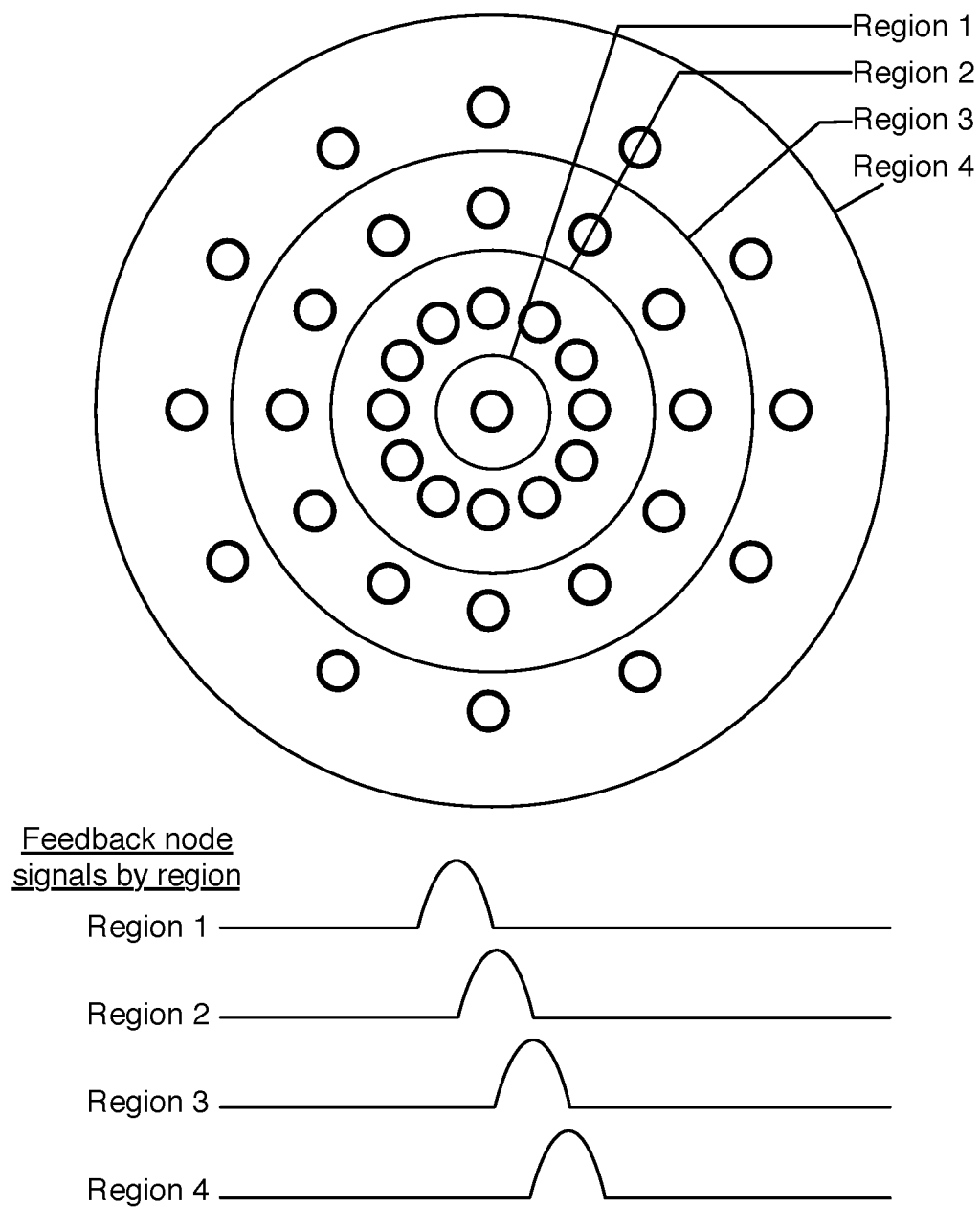
FIGS. 13 and 14 are schematic representations of two variations of sequences of haptic feedback node activation.
Figure 14:
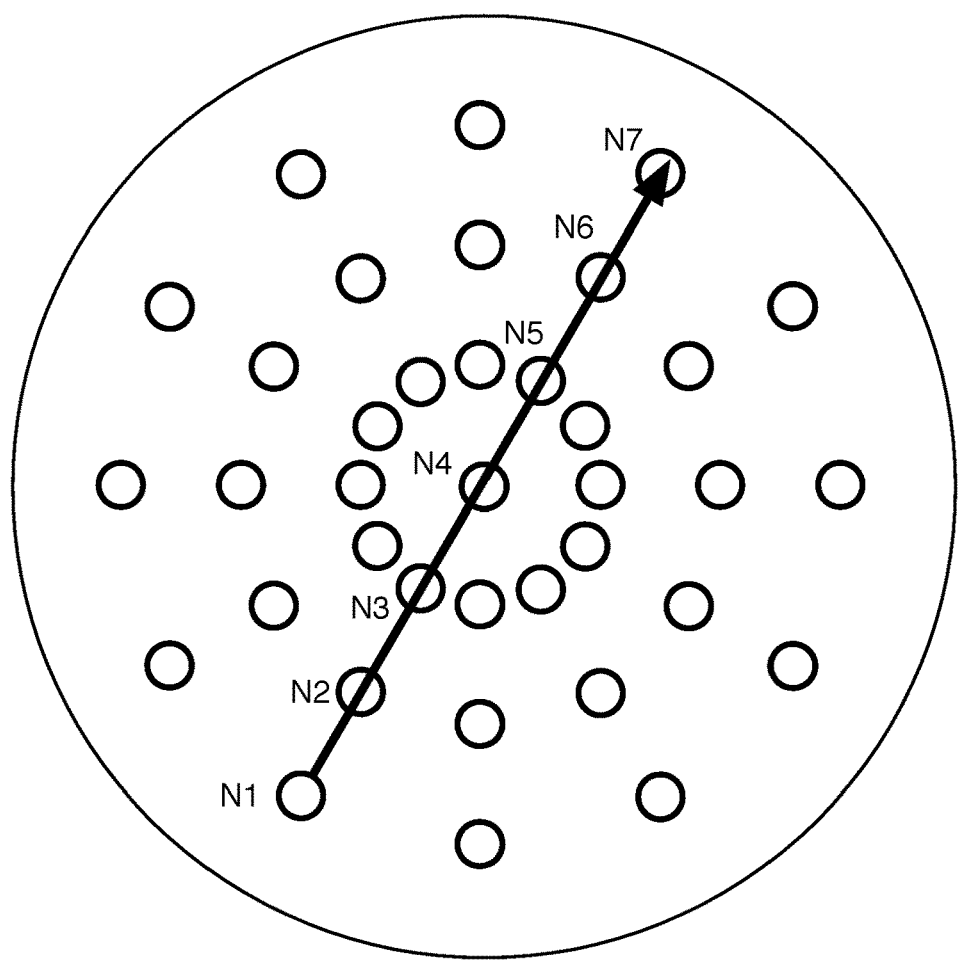
Figure 14:
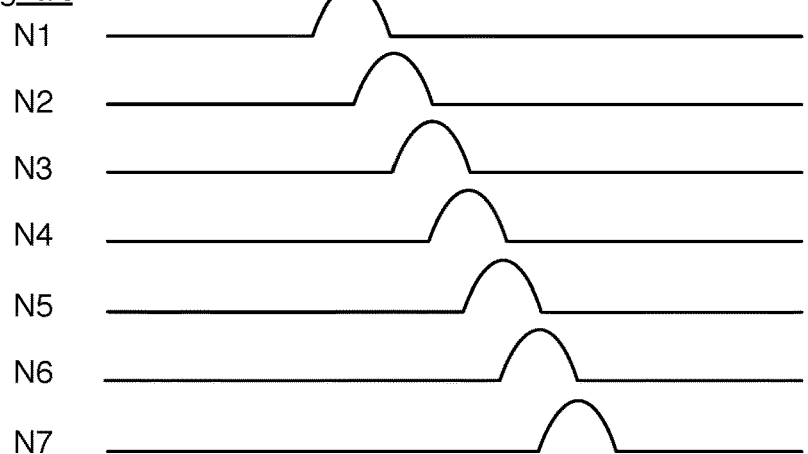

In another variation, the activation sequence of a set of haptic feedback nodes 132 can simulate motion. The haptic feedback system 130 can be driven in a sequence across an array of feedback nodes, which functions to feel like movement of the vibration. The speed of the motion, the simulated displacement (e.g., the set of feedback nodes used in the activated sequence), the shape or stroke path of sequential node activation, and other properties can be used to signal different information to the user. In a 2D array haptic feedback variation, the vibratory output can initiate at the center and expand from a smaller area to a larger area of the array depending on the biosignal properties as shown in FIG. 13. In another variation, the 2D array haptic feedback system 130 can simulate motion along a vector as shown in FIG. 14. To the user, the motion may feel like a swiping motion in different directions. The magnitude, direction, and angle of the swipe motion can all be used to convey information.

Figure 15:
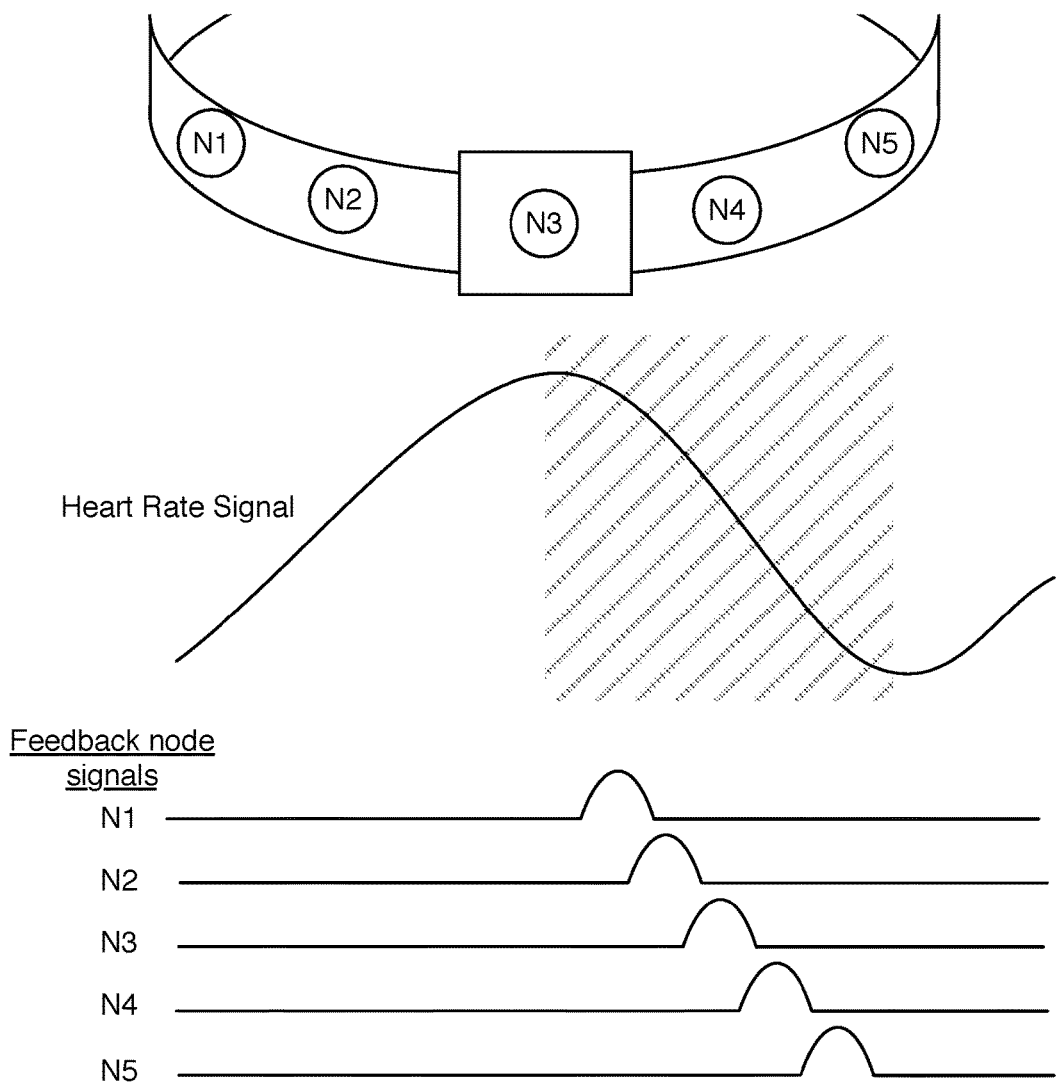
FIG. 15 is a schematic representation of a sequence of haptic feedback node activation synchronized to a biosignal.

In one variation, the activation of the haptic feedback system 130 is in synchronization with a biosignal. Preferably, the haptic feedback system 130 is synchronized to the declining portion of the HRV periodic signal as shown in FIG. 15, which functions to synchronize the user's focus with the breath. The haptic feedback system 130 can be activated at substantially the local maximum of the heart rate signal and then sustained until the local minimum of the heart rate signal. This window of the heart rate signal can correlate to the outward/exhaling breath of a user. A user can be reminded to breathe outward during this window. The activation of the haptic feedback system 130 can additionally offset the activation window to the biosignal. This can be used to promote longer or shorter breaths.

Figure 16:
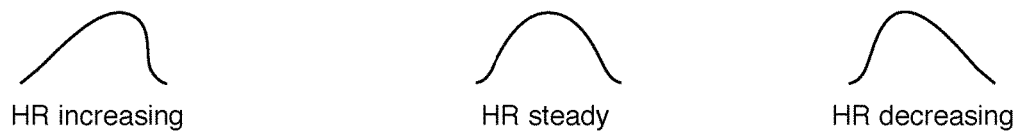
FIG. 16 is a schematic representation of various haptic feedback shape profiles.
Figure 16:
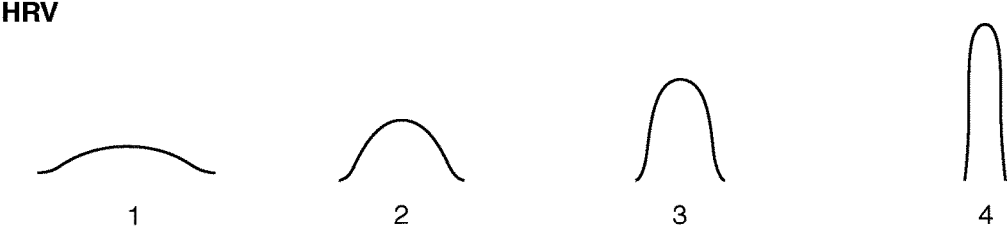
Figure 16:
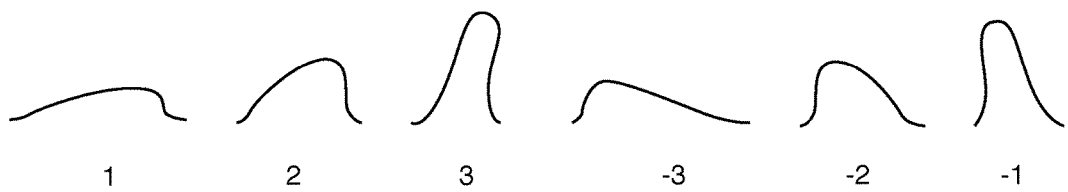

In another variation, the activation of the haptic feedback system 130 can activate a particular form, shape, or path to communicate various forms of information. In one implementation, the duration, magnitude and profile of a path can be used to convey different information. As shown in the first row of FIG. 16, a bell curve path may lean one direction or another based on the amount to which a user's heart rate is changing. This path could be activated in a multi-directional haptic feedback system 130 such as the ones shown in FIGS. 10 and 11. The path could be synchronized to actuate on every heart beat, every breath, or at any suitable time. As also shown, the intensity and duration of a pulse path can be mapped to the HRV of a user. For example, the intensity could be increased and the duration decreased to reflect a higher HRV, and a low HRV would be longer and less intense pulse as shown in the second row of FIG. 16. Additionally, multiple forms of biosignal feedback can be layered into a single haptic pattern. As shown in the last row FIG. 16, heart rate and HRV feedback can be layered.

The computing system 140 can additionally be distributed between multiple devices. In one variation, the computing system 140 includes a first device computing system integrated in the attachment structure 110 and a second user interface application operable on a second device and in communication with the first device. The first device computing system can facilitate sensing and haptic feedback, which the user interface application portion provides operability on a personal computing device. The user interface application can additionally function to provide additional user interface options. The user interface application is preferably operable on a personal computing device such as a smart phone, a tablet, a wearable computer, a desktop computer, and/or any suitable computing device. The user interface application can provide access to graphical user interface, auditory cues, device haptic feedback, and other forms of user interfaces. The device worn by the user can be in communication with the device of the user interface application. The user interface application can be used to show historical data, receive user input, and perform any suitable task.

Figure 17:
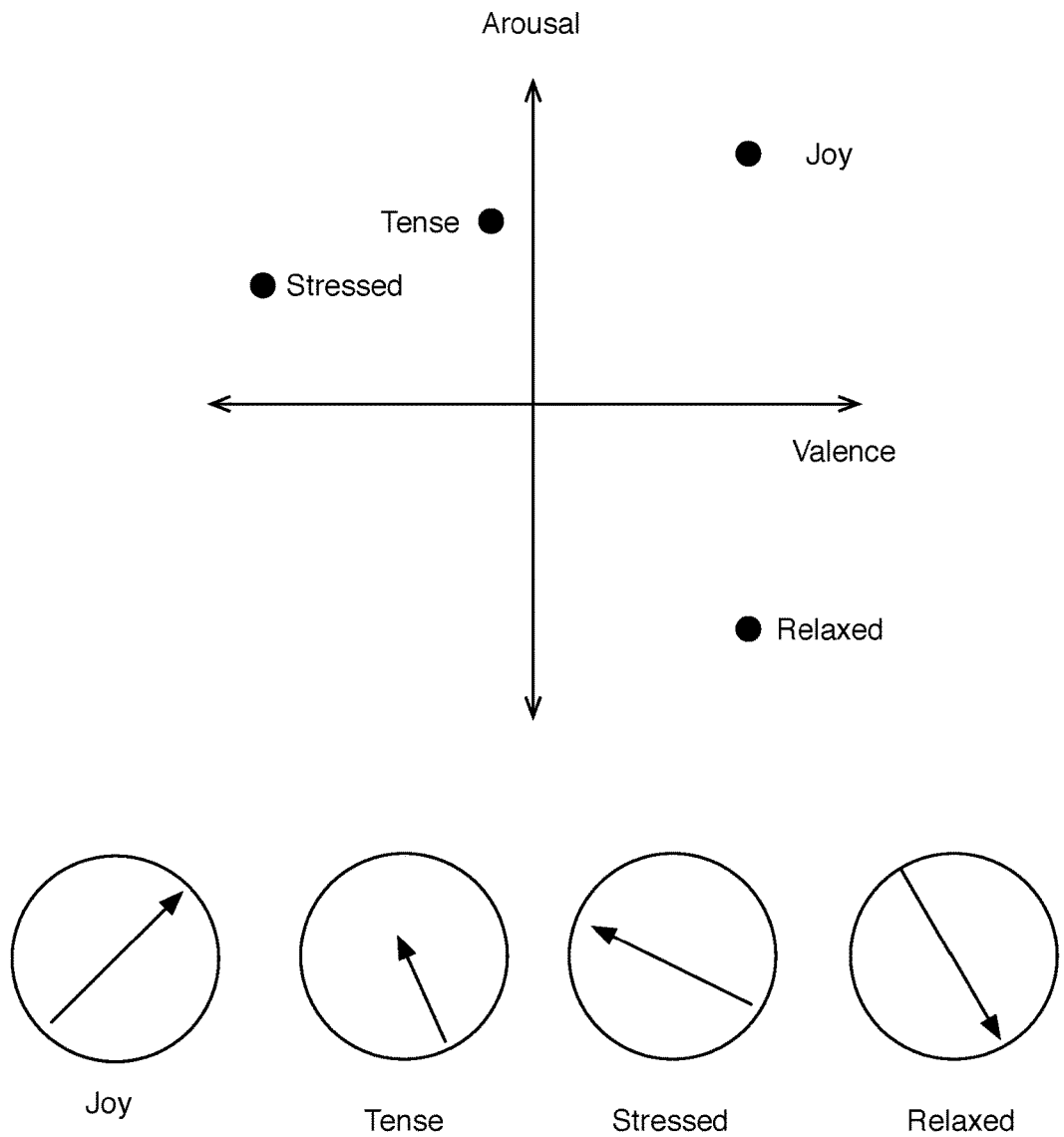
FIGS. 17 and 18 are schematic representations of haptic feedback node activation mapped to an emotional coordinate system.
Figure 18:
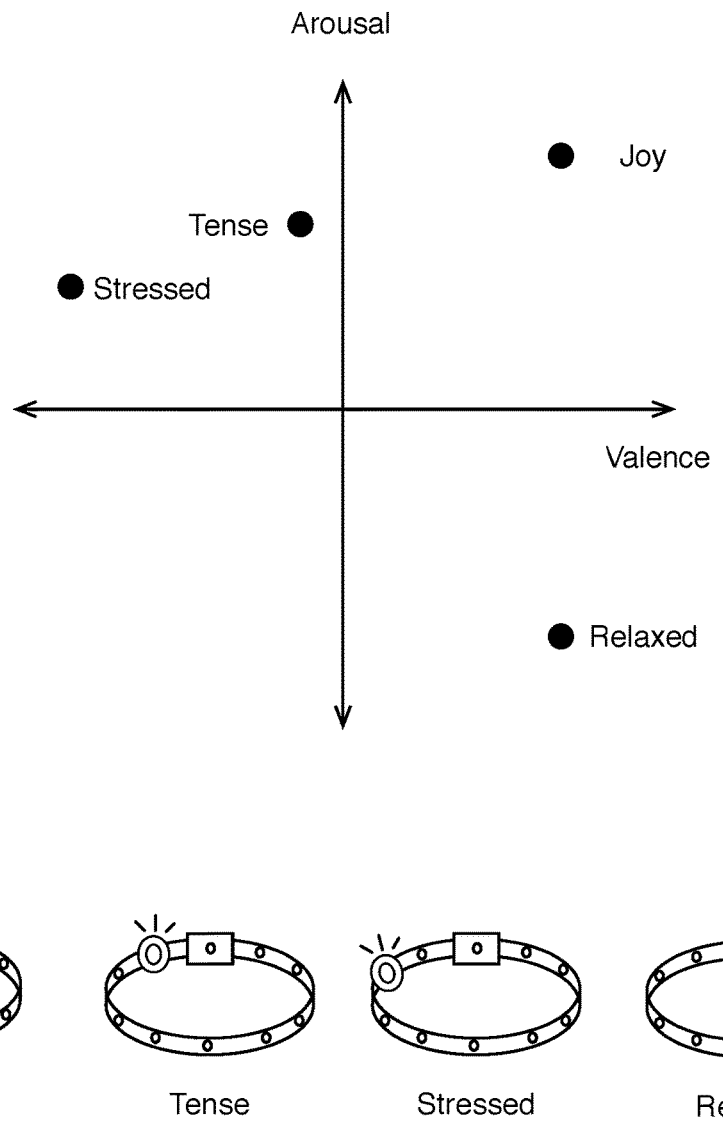

In one variation, the user interface application can include an emotional tracking module that is configured to collect emotional state information or other forms of emotional data from the user. The emotional tracking module is additionally configured to log that information. The system 100 can generate a model between emotional state and the collected physiological data to automatically predict emotional state based on collected physiological data. The model can be used to activate the haptic feedback system 130 in response to the predicted current emotional state so as to communicate the current predicted emotional state to the user. The emotional state can be communicated using a variety of activation options of the haptic feedback system 130. One preferred implementation uses maps the predicted emotional state to an emotional coordinate system. One common emotional coordinate system is a valence and arousal coordinate system. The haptic feedback system can be driven to simulate a vector that corresponds to the predicted emotional state plotted on the emotional coordinate system. Magnitude and angle can both be communicated in a 2D array feedback system as shown in FIG. 17. Alternatively, the mapping to the emotional coordinate system may be reduced to an angular representation so as to be communicated through a 1D array feedback system as shown in FIG. 18.

2. Method for Communicating Biofeedback to a User

Figure 19:
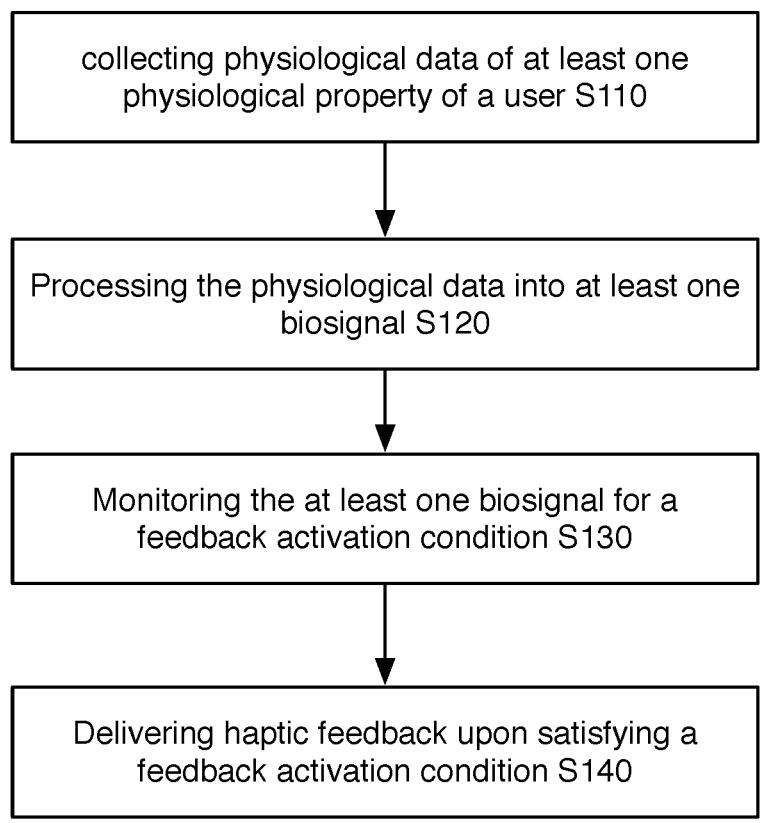
FIG. 19 is a flowchart representation of a method of a preferred embodiment.

As shown in FIG. 19, a method for augmenting a biosignal through active feedback of a preferred embodiment can include collecting physiological data of at least one physiological property of a user S110, processing the physiological data into at least one biosignal S120, monitoring the at least one biosignal for a feedback activation condition S130, and delivering haptic feedback upon satisfying a feedback activation condition S140. The method functions to provide real-time unobtrusive feedback to a user based on physiological properties. The method is preferably used to promote awareness of a user's physiological state. Many biological signals are not readily detectable by a person. Generally, the method can enable an individual to build real-time awareness of their state, which can function to promote mindfulness in a user. In some cases, a user may be able to use this awareness to address their mental state through mental exercises, breathing exercises, physical exercises, meditation, or any suitable action. In time, a user may be able to regulate and control the biosignal to some degree based on trained mindfulness.

More specifically, the method can be applied to coach a user in practicing breathing exercises or performing other actions at appropriate times based on the biosignal information. For example, the method can be used to coach a user to breathe out in synchronization with their heart rate variability signal.

The method can additionally have applications to medical treatment. For example, a therapist could be outfitted with a device with the haptic feedback system while a biosensor measures the physiological data on a patient. The therapist could have an awareness of the patient's physiological state during a therapy session, which can be applied in how the patient is treated.

In yet another variation, the method can include tracking of emotional state, which can be used in automatic detection of emotional state after collection of sufficient data. The haptic feedback can then be used to signal a detected emotional state to a user.

The method is preferably implemented by a system such as the one described above, but the method may alternatively be implemented by any suitable system. In one variation, the method may be applied within a smart wearable that includes access to a biosensor and a haptic feedback mechanism. The smart wearable can additionally include a communication channel to a biosensor or a haptic feedback mechanism.

Block S110, which includes collecting physiological data of at least one physiological property of a user, functions to collect information of at least one health vital property.

The physiological property is preferably heart rate activity. Heart rate data can be collected by an ECG sensor, an electroencephalogram (EEG) sensor, an electromyography (EMG) sensor, a galvanic skin response (GSR) sensor, a photoplethysmography (PPG) sensor, an infrared spectroscopy (NIRS) sensor, a photoplethysmography (PPG) sensor, and/or any suitable type of heart rate detection device. The biosignal may alternatively be breathing rate collected by breath sensor. The heart activity data is preferably collected with a sampling resolution sufficient to produce a real-time analysis of heart rate variability. The sampling frequency of instantaneous heart activity is preferably at least twice that of expected heart rate variability frequency. The physiological data can include any additional or alternative health vitals or signals. The physiological data is preferably sensed from a senor on the device. The physiological can additionally be a composite of sensor data from a variety of sample points on the body. Collecting physiological data can include sensing data from a biosensor. Alternatively, collection physiological data can include retrieving data from a secondary device such as through a communication. For example, a second device, such as a smart watch, may collect heart rate data, and the heart rate data can be communicated to an application or device of the method.

Block S120 and S130, which include processing the physiological data into at least one biosignal and monitoring the at least one biosignal for a feedback activation condition, functions to analyze and monitor the biosignal for various conditions. Preferably, the biosignal is a heart rate signal. The heart activity data can be processed into a heart rate signal. The heart rate signal preferably corresponds to the breathing patterns of an individual. Thus processing the physiological data can additionally include generating breathing data. The breathing data can include breathing rate, instant or average duration of an inhaling breath, instant or average duration of an exhaling breath, average or instant time between breathing, breathing out/in duty cycle, or other suitable properties of breathing.

Collected physiological data is preferably collected and processed into a biosignal for real-time monitoring. One or more biosignals can be monitored for satisfying feedback activation conditions. The feedback activation condition can be any suitable heuristic or algorithmically determined condition that may trigger some form of haptic feedback. The heuristic-based condition could be customized by a user through configuration user interface element. The feedback activation condition may alternatively be automatically set. For example, a machine learning system can be trained in detecting the emotional state of a user based on previous biosignal and emotion state data.

The condition is preferably the heart rate variance as detected in the heart rate signal falling below a minimum heart rate variability threshold. When the heart rate variability of an individual goes below a minimum threshold, then the user is notified through haptic feedback. The condition could alternatively depend on other factors such as other biosignals, geographic location of the user, inputs provided by a secondary device, or any suitable inputs. In one variation, the method can include collecting IMU data from the device or a personal computing device and classifying the activity level of a user from the IMU. The activity level can be used to determine how a biosignal is analyzed. For example, if a user is performing strenuous activity, then the heart rate variability threshold condition can be changed to account for the physical activity.

Block S140, which includes delivering haptic feedback upon satisfying a feedback activation condition, functions to activate the feedback mechanism in a meaningful manner. Haptic feedback is preferably delivered in a variety of different conditions. Haptic feedback can be delivered when a biosignal is detected to be above or below a particular threshold. Haptic feedback can additionally be delivered when the pattern of one or more biosignals is detected to have a high correlation to a particular pattern. For example, machine learning could be used to correlate biosignals with emotional state (as reported by a user) and then used in automatic detection of emotional state.

Delivering haptic feedback upon satisfying a feedback activation condition can include mapping between a value of one or more biosignals and the activation of a pattern of haptic feedback which functions to deliver haptic feedback in an activation mode corresponding to the context of the biosignal. For example, the pattern of feedback may be changed to indicate different conditions or properties of the condition (e.g., the magnitude of HRV, the type of emotion, etc.). The context may depend on a classification determined in block S120, the magnitude of a measurement from block S120 (e.g., the amount over a HRV threshold), and/or any suitable property. In one variation, the haptic feedback is consistently delivered based on the values of the biosignal.

In one variation, delivering haptic feedback can include synchronizing haptic feedback to a biosignal, which functions to time the haptic feedback with the periodic properties of a biosignal. Preferably, activate feedback is synchronized to the hear rate signal as shown in FIG. 15. In this variation, synchronizing haptic feedback to the heart rate signal comprises initiating haptic feedback in coordination with a local maximum of the heart rate signal and ending haptic feedback in coordination with a local minimum of the heart rate signal, which functions to stimulate the user periods that correlate with an exhaling breath. Applying haptic feedback in synchronization with a user's breathing can increase awareness to achieve a level of mindfulness.

Synchronizing the haptic feedback can additionally include augmenting the timing of the haptic feedback in coordination with the local maximum and minimum of the signal. In one implementation, this may be done to promote a breathing pattern objective. The method can include determining a breathing pattern objective, which may be based on the current physiological conditions, physiological history, or any suitable property. Augmenting the timing may include offsetting the initiation before or after the local maximum HRV. Similarly, timing may include offsetting the ending of haptic feedback to before or after the local minimum. Augmenting the activation window (e.g., the period of haptic feedback between activation and ending) can encourage different breathing patterns. These adjustments can be made to reinforce longer breaths, shorter breaths, speeding up breathing rate, slowing down breathing rate, breathing in a particular pattern, or making any suitable change to breathing. For example, if a user is taking short breaths, then the method may augment the timing of synchronized haptic feedback so that the user is reminded to take longer breaths.

In another variation, delivering haptic feedback can include activating a sequence of haptic feedback nodes 132 in coordination with the biosignal. The intensity (i.e., magnitude) and timing of haptic feedback node activation can be used to convey different information or to deliver different tactile feelings. In one implementation, an array of haptic feedback nodes 132 is activated in a progressive pattern to simulate motion across the array. The sequence can be a linear pattern, radial pattern, along a vector or path, or in any suitable animated sequence. The progressive sequence can progress according to an easing function (e.g., ease-in, ease-out, bounce, etc.), repeat, change intensity as a function of time, or augment any suitable property of sequential activation. The properties of the sequential activation can correlate to various properties and can be used to signal different information to the user. In the synchronized haptic feedback variation above, delivering synchronized haptic feedback can include activating haptic feedback nodes 132 of an array in a progressive sequence. In one example, the sequence of activation can initiate during the beginning of an exhale (e.g., at a local maximum HRV) and attenuate until the activation ends at the end of the exhale window. This activation intensity profile can be adjusted to promote different breathing patterns. For example, if the user is not breathing out for the full duration, the intensity may increase to encourage the user to make it to the end of the desired exhaling window.

Preferably, delivering haptic feedback is delivered to the user corresponding to the biosignals. However, some variations, may deliver haptic feedback to at least a second user, which can function to provide a physiological form of communication between the first and second user. This may be used during therapy treatment. For example, a therapist could receive haptic feedback based on the emotional and/or physiological state of a patient. Similarly, couples or two people could use the device during a conversion, which may promote improved empathy or communication.

As discussed above, one embodiment of the method can include retrieving emotional state data over a period of time S150 and predicting the emotional state according to the retrieved emotional state data and collected physiological data S132. In this variation, haptic feedback can be delivered according to detection of emotional state. The feedback activation condition is prediction of at least one particular emotional state. Processing of the biosignal can include training an algorithmic model from the retrieved emotional state data and the biosignal and automatically predicting emotional state in real-time from the algorithmic model. Other approaches may alternatively be used such as heuristic based emotional state prediction.

Emotional state data is preferably retrieved through a user interface. The user interface can be personal computing device, a web application, a communication tool, or any suitable interface through which emotional information is collected. A user will preferably periodically log how they feel. In one variation, the user will log a particular feeling such as happy, sad, stressed, anxious, angry, and the like. In another variation, the user will provide a rating along one or more emotional dimensions. The user may additionally provide comments or supply emotional data through any suitable mechanism.

Figure 20:
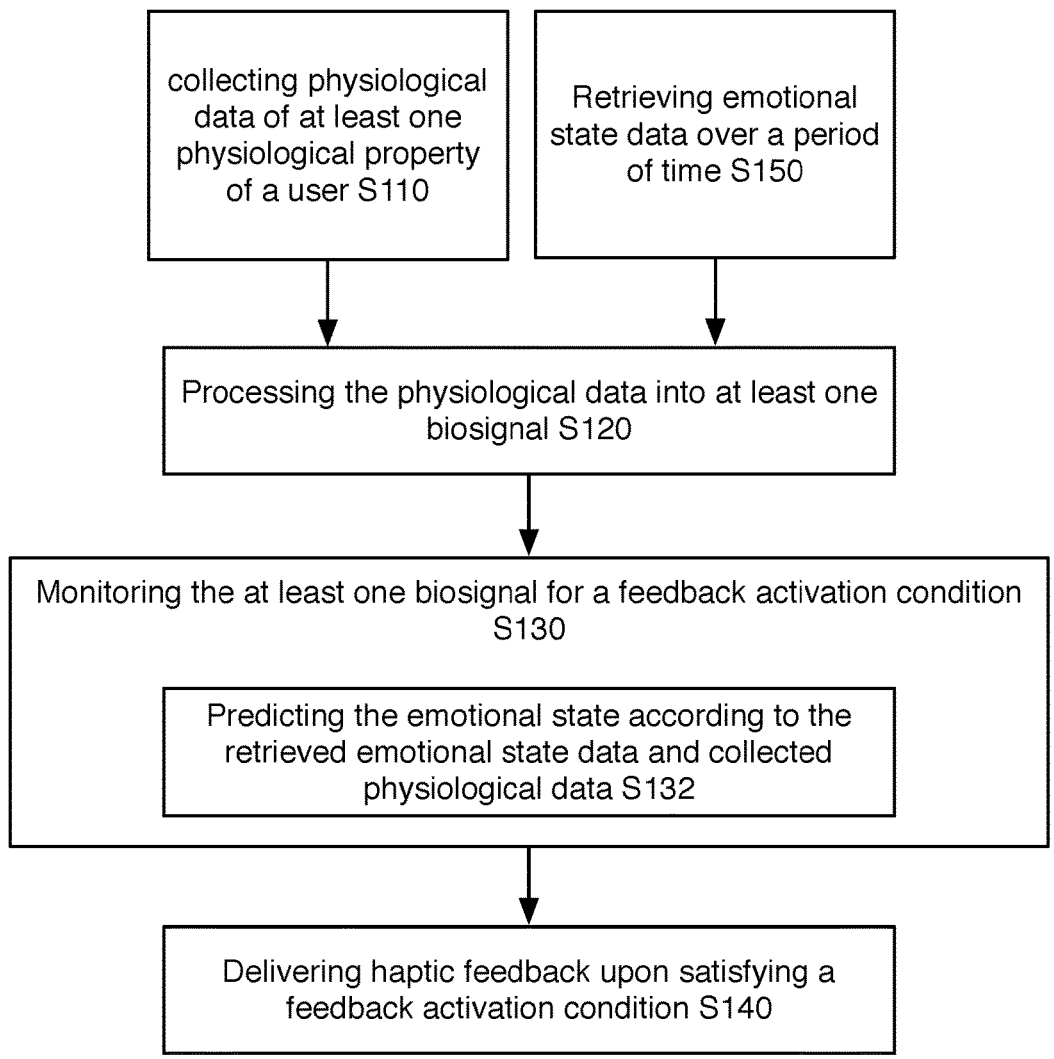
FIG. 20 is a flowchart representation of a variation of a method of a preferred embodiment.

In one variation, a predicted emotional state is mapped an emotional coordinate system such as a coordinate system with arousal and valence as the two orthogonal dimensions. The arousal and valence dimensions can be used to characterize a variety of emotions. Delivering the haptic feedback comprises activating at least one of an array of haptic feedback nodes according to the mapping of the emotional state to the emotional coordinate system S132 as shown in FIG. 20. In a 2D array of haptic feedback nodes, an activation sequence simulates the direction and magnitude of a vector corresponding to the position of the emotion in the emotional coordinate system as shown in FIG. 17. For example joy can be classified as high valence (i.e., positive) and high arousal so the sequence of activating haptic feedback nodes would be a long stroke in the first quadrant. Similarly, tense may be slightly negative valence and medium level of arousal so the sequence of activating haptic feedback nodes would be a medium length stroke upward and slightly to the right. In a 1D array of haptic feedback, the haptic feedback may be reduced to the angular position of the predicted emotion in the emotional coordinate system. As shown in FIG. 18, the angle of the vector to the emotion in the emotional coordinate system can be represented in which node is activated. Joy may be felt in the front right of the body, relaxation would be in the back right, and stressed would be on the left front.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for communicating biofeedback to a user through a wearable device to guide the breathing of the user comprising:
   at the wearable device, collecting physiological data of the user, wherein the physiological data includes at least heart rate data;
   processing the physiological data into a set of biosignals, wherein the set of the biosignals comprises of at least a heart rate signal;
   monitoring the set of the biosignals for a feedback activation condition, wherein the feedback activation condition is based on at least the variance of the heart rate signal; and
   upon satisfying the feedback activation condition, delivering a haptic feedback at the wearable device, which comprises initiating the haptic feedback in coordination with a local maximum of the at least the heart rate signal and ending the haptic feedback in coordination with a local minimum of the at least the heart rate signal.

2. The method of claim 1, further comprising determining a breathing pattern objective; wherein initiating the haptic feedback in coordination with the local maximum comprises augmenting timing of initiating the haptic feedback according to the breathing pattern objective; and wherein ending the haptic feedback in coordination with the local minimum comprises augmenting timing of ending the haptic feedback according to the breathing pattern objective.

3. The method of claim 1, wherein delivering the haptic feedback comprises activating a sequence of haptic feedback nodes in synchronization with a heart rate variability in the heart rate signal.

4. The method of claim 3, wherein activating the sequence of haptic feedback nodes comprises setting timing and intensity of activation according to the properties of the haptic feedback condition.

5. The method of claim 1, wherein delivering the haptic feedback comprises delivering the haptic feedback according to predicted emotional state based in part on the processed physiological data.

6. The method of claim 5, further comprising retrieving emotional state data over a period of time, predicting the emotional state according to the retrieved emotional state data and collected physiological data; and wherein the feedback activation condition is further based on a prediction of at least one particular emotional state.

7. The method of claim 6, further comprising mapping the predicted emotional state to an emotional coordinate system; and wherein delivering the haptic feedback comprises activating at least one of an array of haptic feedback nodes according to the mapping of the emotional state to the emotional coordinate system.

8. A system for communicating biofeedback to a user through a wearable device comprising:
- a heart activity sensor that collect heart rate data of the user;
- a haptic feedback system;
- a computing system that generates at least one biosignal based on the collected heart rate data, wherein the at least one biosignal includes a heart rate signal, and wherein the computing system is operable to manage an activation of the haptic feedback system based in part on a heart rate variability in the heart rate signal; and wherein the computing system includes configuration to initiate the haptic feedback in coordination with a local maximum of the heart rate signal and end haptic feedback in coordination with a local minimum of the heart rate signal.

9. The system of claim 8, wherein the haptic feedback system includes an array of haptic feedback nodes.

10. The system of claim 9, wherein the haptic feedback nodes of the array of haptic feedback nodes are distributed across at least two dimensions.

11. The system of claim 9, wherein the computing system can set the haptic feedback system into an activation mode that sequentially activates a subset of haptic feedback nodes in the array of haptic feedback nodes.

12. The system of 8, wherein the haptic feedback system includes at least one type of haptic feedback node selected from the set of a vibrational feedback node, a protruding feedback node, and a tapping feedback node.

13. The system of claim 8, further comprising at least one attachment structure that houses a subset of components of the system, wherein the at least one attachment structure can be physically coupled to the body of the user.

14. The system of claim 13, wherein the at least one attachment structure can be one of a chest band, a wristband, and an undergarment.

* * * * *